United States Patent
Fowler et al.

(10) Patent No.: US 11,242,419 B1
(45) Date of Patent: *Feb. 8, 2022

(54) INTEGRATED PROCESS FOR PRODUCING PROPYLENE POLYMERS AND COPOLYMERS WITH REDUCED GREENHOUSE GAS EMISSION

(71) Applicant: REXtac, LLC, Odessa, TX (US)

(72) Inventors: James Nicholas Fowler, Odessa, TX (US); Deborah Lawrence, Westworth Village, TX (US); Stephen Craig McHaney, Odessa, TX (US)

(73) Assignee: REXtac, LLC, Odessa, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/016,352

(22) Filed: Sep. 9, 2020

(51) Int. Cl.
*C08F 10/06* (2006.01)
*C07C 2/84* (2006.01)
*C07C 6/04* (2006.01)
*C07C 2/08* (2006.01)
*C07C 7/00* (2006.01)
*C07C 7/09* (2006.01)

(52) U.S. Cl.
CPC .............. *C08F 10/06* (2013.01); *C07C 2/08* (2013.01); *C07C 2/84* (2013.01); *C07C 6/04* (2013.01); *C07C 7/005* (2013.01); *C07C 7/09* (2013.01)

(58) Field of Classification Search
CPC .... C07C 2/82; C07C 2/84; C07C 2/06; C07C 7/005; C07C 7/04; C07C 11/04; C07C 11/06; C07C 11/08
See application file for complete search history.

(56) References Cited

U.S. PATENT DOCUMENTS

2019/0119182 A1* 4/2019 McCormick .............. C07C 2/84

\* cited by examiner

*Primary Examiner* — Thuan D Dang
(74) *Attorney, Agent, or Firm* — Terrile, Cannatti & Chambers; Michael Rocco Cannatti

(57) ABSTRACT

A substantially zero-carbon-emission (ZCE) process for making propylene polymers and copolymers including: converting alkanes to the olefin monomers ethylene, propylene, and butene or combinations thereof, using renewable electric power and scrubbing the stack gases from any fired heaters or boilers to remove carbon dioxide, in an oxidative-coupling of methane plant including the steps of passing alkanes through an ethylene plant while adding oxygen, passing a portion of the polymerization grade ethylene through a 2-butene plant, and passing the 2-butene stream and a portion of the polymerization grade ethylene stream through a propylene plant. The polymerization grade propylene is polymerized to produce isotactic homopolymer polypropylene, or ethylene-propylene random copolymer, or impact grade polypropylene containing ethylene-propylene rubber.

8 Claims, 2 Drawing Sheets

INTEGRATED PROCESS FOR PRODUCING PROPYLENE POLYMERS AND COPOLYMERS WITH REDUCED GREENHOUSE GAS EMISSION

BACKGROUND OF THE INVENTION

Field of the Invention

The present invention relates to processes and systems for the production of olefins and olefin derivatives from alkanes. The present invention further relates to environmentally-friendly processes and systems for the production of olefins and olefin derivatives that emit substantially zero carbon dioxide into the atmosphere.

Description of the Related Art

A need exists for chemical processes with reduced carbon dioxide emissions. A further need exists for chemical processes to produce alkene monomers, used to produce various polymers, with reduced carbon dioxide emissions. The present embodiments meet these needs.

BRIEF DESCRIPTION OF THE DRAWINGS

The present invention may be understood, and its numerous objects, features and advantages obtained, when the following detailed description of a preferred embodiment is considered in conjunction with the following drawings.

DETAILED DESCRIPTION

Figure 1:
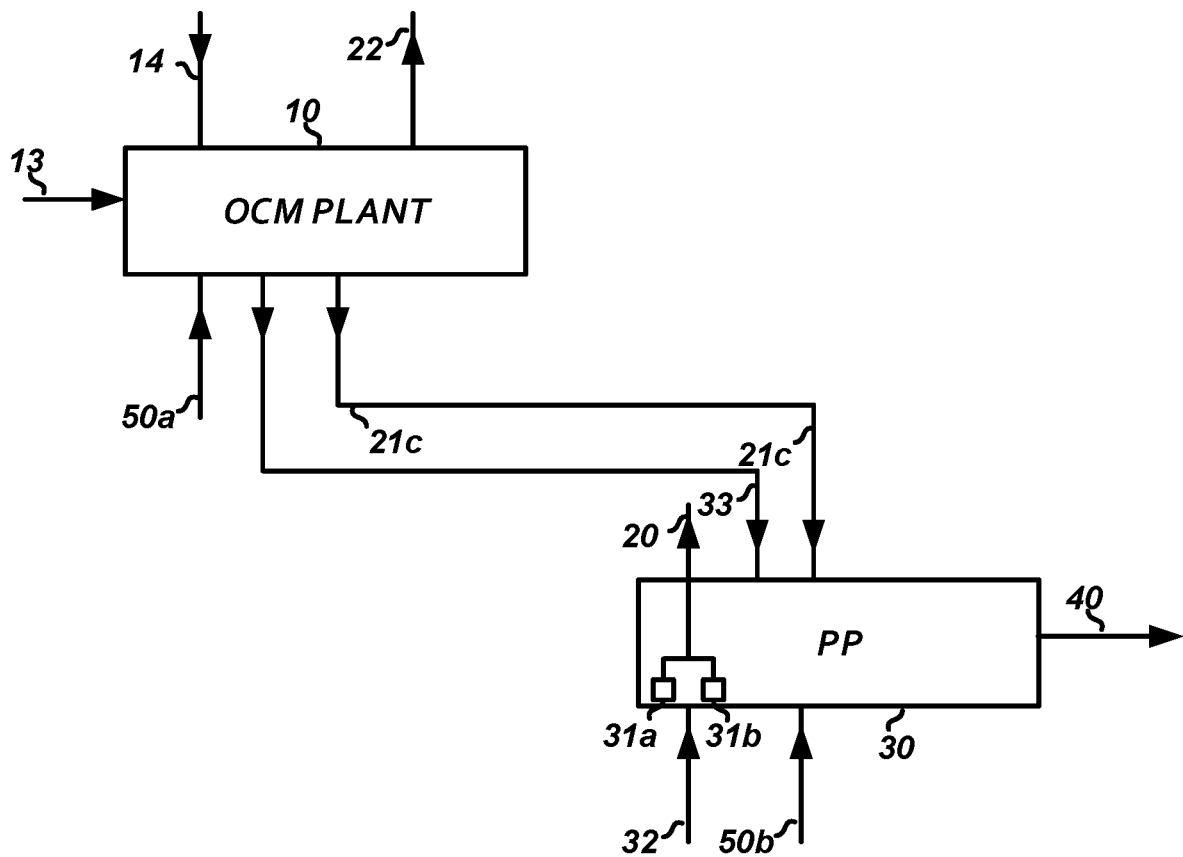
FIG. 1 depicts a substantially zero-carbon-emission process according to one or more embodiments.

Before explaining the present invention in detail, it is to be understood that the invention is not limited to the particular embodiments and that it can be practiced or carried out in various ways.

Specific structural and functional details disclosed herein are not to be interpreted as limiting, but merely as a basis of the claims and as a representative basis for teaching persons having ordinary skill in the art to employ the present invention.

The following description of the embodiments is merely exemplary in nature and is in no way intended to limit the subject matter of the present disclosure, their application, or uses.

The present invention relates to a substantially zero-carbon-emission process for making propylene polymers and copolymers.

The substantially zero emission process includes converting alkanes to the olefin monomers ethylene, propylene, and butene or combinations thereof using renewable electric power in an oxidative-coupling of methane (OCM) plant.

The steps include using an ethylene plant to make ethylene from a natural gas with oxygen.

The steps include using a 2-butene plant to dimerize the ethylene to create 2-butene.

The steps include using a propylene plant to convert the 2-butene stream and some of the ethylene to form propylene.

The steps include polymerizing the propylene and optionally the ethylene in a polypropylene plant to produce isotactic homopolymer polypropylene, or random ethylene-propylene copolymer, or impact-grade polypropylene containing ethylene-propylene rubber made in a second polymerization reactor.

The steps include using renewable electric power while scrubbing the stack gasses from any fired heaters or boilers with a solvent to remove the carbon dioxide.

This integrated process results in substantially zero carbon emissions into the atmosphere to produce propylene polymers and copolymers.

The process of converting alkanes to olefin monomers ethylene, propylene, and butene or combinations thereof uses the renewable electric power 50a in an oxidative-coupling of methane (OCM) plant while additionally recycling a stream of unconverted methane 51 from the first fractionation train to the oxidation reactor.

The process of converting alkanes to olefin monomers ethylene, propylene, and butene or combinations thereof uses renewable electric power in an oxidative-coupling of methane (OCM) plant while additionally recycling a stream of unconverted ethylene 55 from a second fractionation train to a dimerization unit.

The process of converting alkanes to olefin monomers ethylene, propylene, and butene or combinations thereof uses renewable electric power in an oxidative-coupling of methane (OCM) plant while additionally recycling a stream of unconverted ethylene and butene 57 from a third fractionation train to a metathesis reactor.

An ethylene plant to make ethylene includes the steps of contacting a catalyst in an oxidative reactor with oxygen and a natural gas mixture of alkanes producing a mixture of olefin monomers wherein the catalyst is a member of the group consisting of: a lanthanide series metal supported catalyst and an actinide series metal supported catalyst and the catalysis is performed at a pressure from 6 bar to 16 bar and a temperature of 600 to 800 degrees Celsius; and fractionating in a first fractionation train the mixture of monomers forming a first 21a, second 21b, and third 21c polymerization grade ethylene streams and a carbon dioxide stream 22.

The 2-butene plant to convert ethylene to 2-butene includes the steps of dimerizing in a dimerization unit the first polymerization grade ethylene stream 21a to form a stream of butene and by products and fractionating the stream of butene and by products in a second fractionation train forming a pure 2-butene stream 27a.

The propylene plant to convert the 2-butene and some of the ethylene to form propylene includes the steps of reacting the 2-butene stream 27a in a metathesis reactor with the second polymerization grade ethylene stream 21b from the first fractionation train, forming propylene with unconverted ethylene and butene and fractionating the propylene with unconverted ethylene and butene in the third fractionation train forming polymerization grade propylene.

The substantially zero emission process for making propylene polymers and copolymers includes the step of using oxygen enhanced combustion in the hydrocarbon fueled heaters and boilers of the polypropylene plant to limit nitrogen-based gas volumes.

The process is used to make olefin derivatives.
The produced olefin derivative is a poly olefin wax.
The produced olefin derivative is propylene glycol.
The produced olefin derivative is acrylic acid.
The produced olefin derivative is a poly acrylic acid.
The produced olefin derivative is a polyethylene.

One of the reasons this invention is useful is that it sequesters carbon dioxide emissions during the processing of monomers to make olefin derivatives.

The invention not only utilizes renewable energy sources but additionally minimizes the use of fired equipment, and for required fired equipment, scrubs the stack gases from the fired heaters with a solvent to produce propylene polymers and copolymers having a low carbon footprint.

An advantage of the process is that fewer fires can occur because only a limited number of ignition sources are used, improving safety in a plant.

An advantage of the process is that fewer explosions are expected in the chemical plant because electric heaters are not as prone to explode as gas-fired heaters.

The process reduces carbon footprint adjacent to the plant providing cleaner air.

The following terms are defined herein:

The term "2-butene plant" can refer to any of the known technologies for producing 2-butene either by chemical reaction and/or by purification of any stream containing 2-butene. In an embodiment, 2-butene can be produced by dimerization of ethylene followed by purification.

The term "ethylene plant" can refer to any of the known technologies for producing ethylene by the oxidative coupling of methane (OCM), optionally followed by the adiabatic cracking of alkanes, and followed by the capture and sequestration of carbon dioxide from the OCM reactor effluent.

The term "polypropylene" can refer to an isotactic propylene homopolymer or a random ethylene-propylene copolymer or an impact-grade polypropylene containing ethylene-propylene rubber.

The term "olefin monomers" can refer to any alkene containing from two to twelve carbon atoms.

The term "oxidative-coupling of methane (OCM) plant" can refer to the catalytic reaction of methane in the presence of oxygen to produce alkenes.

The term "propylene plant" can refer to any of the known technologies for producing propylene by chemical reaction and/or by purification of any stream containing propylene. In embodiments, propylene can be produced by the metathesis of ethylene and butene.

The term "substantially zero carbon dioxide emission" can refer to reducing the emission of carbon dioxide to the maximum practical extent; limited only by safety and environmental regulations which require the operation of safety and emission-control devices such as flares and thermal oxidizers; and by the fact that all real separation technologies are limited by thermodynamic and chemical equilibria which never achieve a mathematically zero concentration.

As used throughout, ranges are used as shorthand for describing each and every value that is within the range. Any value within the range can be selected as the terminus of the range. Unless otherwise specified, all percentages and amounts expressed herein and elsewhere in the specification should be understood to refer to percentages by weight.

For the purposes of this specification and appended claims, unless otherwise indicated, all numbers expressing quantities, percentages or proportions, and other numerical values used in the specification and claims, are to be understood as being modified in all instances by the term "about." The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of + or −10 percent, alternatively + or −5 percent, and alternatively + or −1 percent of the given numeric value provided such a deviation does not alter the end function or result of the value. Accordingly, unless indicated to the contrary, the numerical parameters set forth in this specification and attached claims are approximations that can vary depending upon the desired properties sought to be obtained by the present invention.

It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. For example, as used in this specification and the following claims, the terms "comprise" (as well as forms, derivatives, or variations thereof, such as "comprising" and "comprises"), "include" (as well as forms, derivatives, or variations thereof, such as "including" and "includes") and "has" (as well as forms, derivatives, or variations thereof, such as "having" and "have") are inclusive (i.e., open-ended) and do not exclude additional elements or steps. Accordingly, these terms are intended to not only cover the recited element(s) or step(s), but may also include other elements or steps not expressly recited. Furthermore, as used herein, the use of the terms "a" or "an" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

The present disclosure is directed to integrated processes for converting alkanes to olefins and olefins to olefin derivatives. In some instances, the alkanes are methane, ethane, propane, butane, and pentane. In other instances, the alkanes can be linear alkanes having six or more carbons. In yet other instances, the alkanes can be branched alkanes having four or more carbons. In some instances, the alkanes can be a mixture of one or more alkanes. When a mixture of one or more alkanes is used, the mixture can be delivered as a stream to a separation system or apparatus such as a fractional distillation apparatus. Separation of the individual alkanes from the mixture of one or more alkanes can take place prior to any of the integrated processes described herein or as a step during any of the integrated processes described herein. In some instances, alkanes for use in the integrated processes described herein, such as methane, can be derived from renewable biologic sources.

In some instances, the olefins produced are ethylene and propylene. In other instances, the produced olefins are any olefin having four or more carbons. In some instances, the produced olefins are any olefin having a terminal alkene. Olefin derivatives produced according to various aspects of the present disclosure can be, for example, a polyalkene such as polypropylene or polyethylene or a polyalkene co- or terpolymer, an amorphous poly alpha olefin, an alkene oxide such as propylene oxide or butylene oxide, a poly olefin wax, a glycol such as propylene glycol or ethylene glycol, an acrylic acid, a poly acrylic acid, or any other desired olefin derivative.

In accordance with various aspects of the present disclosure, integrated processes for converting alkanes to olefins and olefins to olefin derivatives can comprise converting alkanes to olefins and olefins to olefin derivatives, capturing carbon dioxide produced during the conversion of alkanes to olefins and olefins to olefin derivatives, and sequestering the produced carbon dioxide. The carbon dioxide can be produced as a reaction by-product or by one or more systems, apparatuses or components utilized in said integrated processes. Integrated processes according to various aspects of the present disclosure are environmentally friendly as they result in substantially zero carbon dioxide emissions into the atmosphere.

Processes for converting alkanes to olefins and olefins to olefin derivatives in accordance with various aspects of the present disclosure can be conducted using renewable electric power generation for utility electric service.

In some instances, the conversion of alkanes to olefins and olefins to olefin derivatives can comprise converting alkanes to olefins and olefins to olefin derivatives using solar energy, directly or indirectly, as an energy source. In other instances, the conversion of alkanes to olefins and olefins to olefin derivatives can comprise converting alkanes to olefins and olefins to olefin derivatives at elevated temperatures using hydrocarbon fueled heaters and/or boilers as heat sources. Such heat sources can generate numerous carbon and non-carbon containing environmental pollutants such as carbon dioxide. Such environmental pollutants are generally expelled from an industrial worksite, such as a refinery or a chemical plant, in the form of flue gas. In the present disclosure, carbon dioxide in the flue gas is captured and sequestered to result in zero or substantially zero carbon emissions into the atmosphere. In some instances, an alkyl amine is used to capture produced carbon dioxide. The alkyl amine can be any one of a primary, secondary, or tertiary alkyl amine. In some instances, carbon dioxide formed during the conversion of alkanes to olefins and olefins to olefin derivatives is recovered, dried, and compressed prior to sequestration.

In some instances, an oxygen-combustion technique can be used in the hydrocarbon-fueled heaters and boilers to limit nitrogen-based gas volumes. In yet other instances, a synthetic air (that is, a mixture of recycled flue gas and oxygen) combustion technique can be used in the hydrocarbon-fueled heaters and boilers to limit nitrogen-based gas volumes.

According to various aspects of the present disclosure, ethylene, produced from alkanes such as methane, are used to produce other olefins such as propylene or 2-butene. Heat inputs can be supplied with zero carbon emissions through the use of, for example, electric heaters or hydrocarbon-fueled heat sources. Flue gases produced during the production of olefins from ethylene can be stripped of carbon dioxide for drying and compression prior to sequestration.

According to various aspects of the present disclosure, olefin derivatives such as polyalkenes such as polypropylene or polyethylene or polyalkene co- or terpolymers, amorphous poly alpha olefins, alkene oxides such as propylene oxide or butylene oxide, poly olefin waxes, glycols such as propylene glycol or ethylene glycol, acrylic acids, poly acrylic acids, or any other desired olefin derivatives, are produced from olefins. Heat inputs can be supplied with zero carbon emissions through the use of, for example, electric heaters or hydrocarbon-fueled heat sources. Flue gases produced during the production of olefins from ethylene can be stripped of carbon dioxide for drying and compression prior to sequestration.

In some instances, ethylene is produced via the oxidative coupling of methane. When olefins are produced via oxidative coupling of methane, carbon dioxide produced as a by-product during processes of the present disclosure is produced in a separate and concentrated stream and substantially zero flue gas emissions are produced.

Alkanes, olefins and olefin derivatives present in final product mixtures can be separated, by any suitable technique known to one skilled in the art, to yield pure or substantially pure alkanes, olefins, and olefin derivatives for sale or use in any of the integrated processes according to the present disclosure. In some instances, final product mixtures are subjected to a fractional distillation process to isolate alkanes, olefins, and olefin derivatives contained therein. In instances where only olefins are produced, such fractional distillation processes can be used to isolate unreacted alkanes from the olefin product.

Although the present invention and its objects, features, and advantages have been described in detail, other embodiments are encompassed by the invention. Finally, those skilled in the art should appreciate that they can readily use the disclosed conception and specific embodiments as a basis for designing or modifying other structures for carrying out the same purposes of the present invention without departing from the scope of the invention as defined by the appended claims.

FIG. 1 depicts a substantially zero-carbon-emission process for making propylene polymers and copolymers according to one or more embodiments.

The substantially zero-carbon-emission process can convert alkanes 14 to the olefin monomers ethylene, propylene, and butene or combinations thereof using renewable electric power 50a in an oxidative-coupling of methane (OCM) plant 10 by using the following steps:

The steps include using an ethylene plant to make ethylene from a natural gas with oxygen.

The ethylene plant to make ethylene can include fractionating in a first fractionation train 20 the mixture of monomers forming a first 21a, second 21b, and third 21c polymerization grade ethylene streams and a carbon dioxide stream 22.

The steps include using a 2-butene plant to convert the ethylene to produce 2-butene 27a.

The steps include using a propylene plant to convert 2-butene and some of the ethylene 21b to form propylene.

The propylene plant to convert the 2-butene and some of the ethylene to form propylene can include fractionating the propylene with unconverted ethylene and butene in a third fractionation train forming polymerization grade propylene 33.

The substantially zero-carbon-emission process can polymerize propylene and, optionally, the ethylene in Polypropylene Plant 30. Any of the known propylene polymerization technologies may be employed. Any of the known propylene polymers or copolymers may be produced.

Renewable electric power 50b is used to scrub stack gasses 31a and 31b.

This integrated process results in substantially zero carbon dioxide emissions into the atmosphere while producing any type of propylene polymer or copolymer 40.

Figure 2:
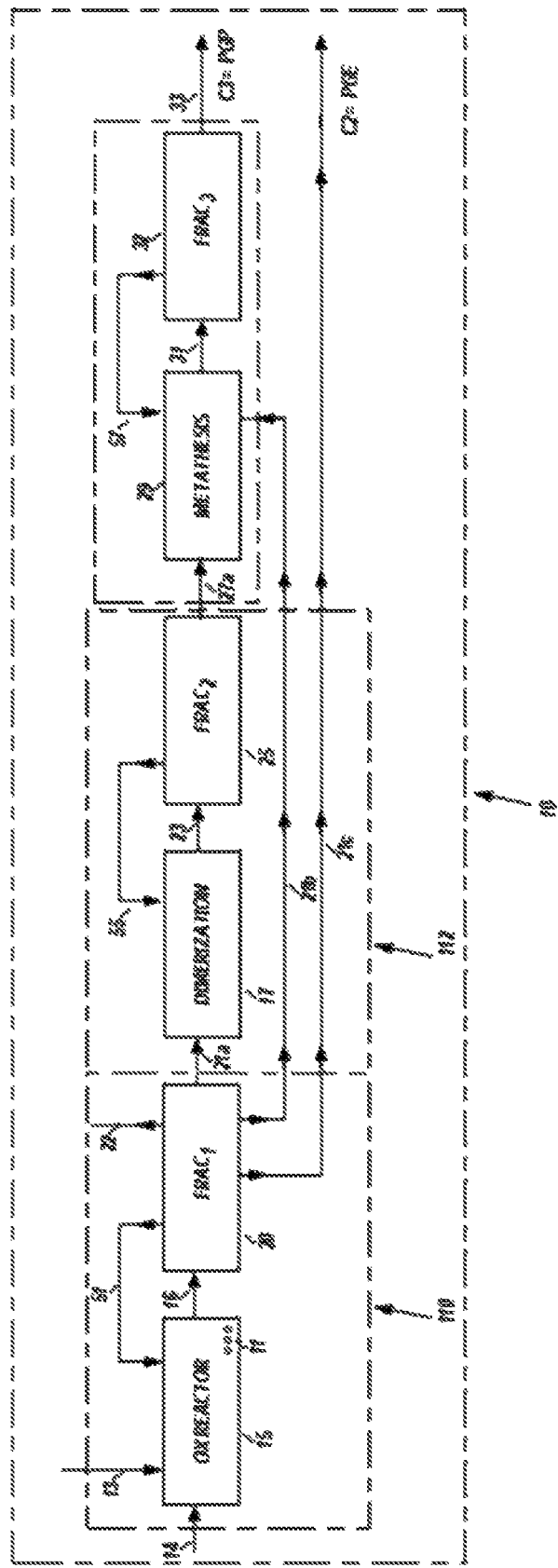
FIG. 2 depicts an oxidative-coupling of methane (OCM) plant according to one or more embodiments.

FIG. 2 depicts an oxidative-coupling of methane (OCM) plant according to one or more embodiments.

The process of converting alkanes 14 to olefin monomers ethylene, propylene, and butene or combinations thereof can use renewable electric power in an oxidative-coupling of methane (OCM) plant 10 while additionally recycling a stream of unconverted methane 51 from the first fractionation train to the oxidation reactor 15.

The process of converting alkanes 14 to olefin monomers ethylene, propylene, and butene or combinations thereof, can use renewable electric power in an oxidative-coupling of methane (OCM) plant 10 while additionally recycling a stream of unconverted ethylene 55 from a second fractionation train 25 to dimerization unit 17.

The process of converting alkanes 14 to olefin monomers ethylene, propylene, and butene or combinations thereof can use renewable electric power in an oxidative-coupling of methane (OCM) plant 10 while additionally recycling a stream of unconverted ethylene and butene 57 from a third fractionation train 32 to metathesis reactor 29.

In embodiments, an ethylene plant 110 to make ethylene can include the steps of: contacting a catalyst 11 in an oxidative reactor 15 with oxygen 13 and a natural gas mixture of alkanes 14 producing a mixture of olefin monomers 16 wherein the catalyst is a member of the group consisting of: a lanthanide series metal supported catalyst and an actinide series metal supported catalyst. The reaction proceeds at a pressure from 6 bar to 16 bar and a temperature of 600 to 800 degrees Celsius; and then the effluent 16 from the oxidation reactor is fractionated in a first fractionation train 20 forming a first, second, and third polymerization grade ethylene streams 21a, 21b, and 21c and a carbon dioxide stream 22.

In embodiments, the 2-butene plant 112 to convert ethylene to 2-butene can include the steps of: dimerizing in a dimerization unit 17 the first polymerization grade ethylene stream 21a to form a stream of butene and by-products 23 and fractionating the stream of butene and by products 23 in a second fractionation train 25 producing a 2-butene stream 27a.

In embodiments, the propylene plant 113, to convert the 2-butene and some of the ethylene to form propylene can include the steps of reacting the 2-butene stream 27a in a metathesis reactor 29 with the second polymerization grade ethylene stream 21b from the first fractionation train forming propylene with unconverted ethylene and 1-butene 31 and fractionating the propylene with unconverted ethylene and 1-butene 31 in a third fractionation train 32 forming polymerization grade propylene 33.

In embodiments, the process can include the step of using oxygen enhanced combustion in the hydrocarbon fueled heaters and boilers of the Polypropylene Plant to limit nitrogen-based gas volumes.

The substantially zero carbon emission process for making olefin monomers can be utilized to produce any of the olefin derivatives.

In embodiments, the produced olefin derivative can be a poly olefin wax.

In embodiments, the produced olefin derivative can be propylene glycol.

In embodiments, the produced olefin derivative can be acrylic acid.

In embodiments, the produced olefin derivative can be a poly acrylic acid.

In embodiments, the produced olefin derivative can be a polyethylene.

Example 1

A substantially zero carbon emission process for making propylene polymers and copolymers includes converting alkanes of natural gas containing methane and ethane to olefin monomers of ethylene, propylene, and butene or combinations thereof using renewable electric power.

In this example, the conversion occurs in an oxidative-coupling of methane (OCM) plant using a combination of wind, and solar power, in a ratio of 80:20 wind to solar power.

As a first step, an ethylene plant is used to make ethylene from the natural gas mixture of methane and ethane.

In this example the natural gas stream has 3% nitrogen, 3% ethane, and the balance of the stream methane. The natural gas stream is reacted with oxygen.

The ethylene can be produced at a rate of 285 kilogram-moles per hour in the OCM plant.

As a second step, a 2-butene plant is used to convert the ethylene to create a 2-butene stream at the rate of 95 kilogram-moles per hour using a fluidly connected dimerization unit and a fractionation train.

As a third step, a propylene plant is used to convert the 2-butene stream and some of the ethylene to form propylene using a metathesis unit and another fractionation train. The conversion can be performed at a rate of 118 kilogram-moles per hour.

As a fourth step, the propylene and, optionally, the ethylene, are polymerized in a Polypropylene Plant.

Renewable electric power usable with this plant's heaters would be the same mix of solar and wind power.

A solvent, such as mono-ethanol amine, can be used to scrub at least one boiler stack gas to sequester carbon dioxide from the boiler stack gas.

This integrated process results in substantially zero carbon emissions into the atmosphere to create olefin monomers that can be polymerized to produce olefin derivatives.

Example 2

A substantially zero emission process for making propylene polymers and copolymers includes converting alkanes of natural gas containing methane, ethane, and nitrogen to olefin monomers ethylene, propylene, butene or combinations thereof using renewable electric power.

In this example, the conversion occurs in an oxidative-coupling of methane (OCM) plant using a combination of wind, and solar power, in a ratio of 50:50 wind to solar power.

As a first step, an ethylene plant is used to make ethylene from the natural gas mixture of methane, ethane and nitrogen.

In this example the natural gas stream has 2% nitrogen, 2% ethane, and the balance of the stream methane. The natural gas stream is reacted with oxygen, which is pure oxygen from an air separation unit.

The ethylene can be produced at a rate of 255 kilogram-moles per hour in the OCM plant.

As a second step, a 2-butene plant is used to convert the ethylene to create 2-butene at a rate of 90 kilogram-moles per hour using a fluidly connected dimerization unit and a fractionation train.

As a third step, a propylene plant is used to convert the 2-butene stream and some of the ethylene to form propylene using a metathesis unit and another fractionation train. The conversion can be performed at a rate of 100 kilogram-moles per hour.

As a fourth step, the propylene and, optionally, the ethylene, are polymerized in a Polypropylene Plant.

Renewable electric power usable with this plant's heaters would be the same mix of solar and wind power.

A solvent, such as methyl diethanol amine (MDEA), can be used to scrub at least one boiler stack gas to sequester carbon dioxide from the boiler stack gas.

This integrated process results in substantially zero carbon emissions into the atmosphere.

Example 3

A substantially zero emission process for making propylene polymers and copolymers includes converting alkanes of natural gas containing methane, ethane, and nitrogen to olefin monomers ethylene, propylene, and butene or combinations thereof using renewable electric power.

In this example, the conversion occurs in an oxidative-coupling of methane (OCM) plant using a combination of wind, and solar power, in a ratio of 100% wind power.

As a first step, an ethylene plant is used to make ethylene from the natural gas mixture of methane, ethane and nitrogen.

In this example the natural gas stream has 2.5% nitrogen, 2.5% ethane, and the balance of the stream methane. The natural gas stream is reacted with oxygen.

The ethylene can be produced at a rate of 275 kilogram-moles per hour in the OCM plant.

As a second step, a 2-butene plant is used to convert the ethylene to create a 2-butene stream at a rate of 100 kilogram-moles per hour using a fluidly connected dimerization unit and a fractionation train.

As a third step, a propylene plant is used to convert the 2-butene stream and some of the ethylene to form propylene using a metathesis unit and another fractionation train. The conversion can be performed at a rate of 125 kilogram-moles per hour.

As a fourth step, the propylene and, optionally, the ethylene, are polymerized in a Polypropylene Plant.

Renewable electric power usable with this plant's heaters would be the same mix of solar and wind power.

A solvent, such as mono-ethanol amine, can be used to scrub at least one boiler stack gasses to sequester carbon dioxide from the boiler stack gas.

This integrated process results in substantially zero carbon emissions to the atmosphere.

By now, it should be appreciated that there has been provided a substantially zero carbon dioxide emissions process, apparatus, and system for making propylene polymers and copolymers. In the disclosed process, alkanes are converted to ethylene, propylene, and butene using renewable electric power in an oxidative-coupling of methane (OCM) plant comprising an ethylene plant, a 2-butene plant, and a propylene plant. The process for converting alkanes includes providing an ethylene plant having an oxidation reactor and a first fractionation train. At the ethylene plant, natural gas and oxygen are converted in the oxidation reactor to produce an oxidation reactor effluent which includes ethylene, and the oxidation reactor effluent is passed to the first fractionation train to recover a first ethylene stream, a second ethylene stream, and a third ethylene stream. In selected embodiments, the process of converting natural gas and oxygen includes contacting a catalyst in the oxidation reactor with oxygen and the natural gas at a pressure from 6 bar to 16 bar and a temperature of 600 to 800 degree C. to produce the oxidation reactor effluent, wherein: (i) the catalyst is selected from the group consisting of a lanthanide series metal supported catalyst and an actinide series metal supported catalyst; (ii) the natural gas comprises a mixture of alkanes; and (iii) the oxidation reactor effluent comprises ethylene and carbon dioxide. The process for converting alkanes also includes providing a 2-butene plant having a dimerization unit and a second fractionation train. At the 2-butene plant, a portion of the first ethylene stream is converted in the dimerization unit to produce a dimerization unit effluent which includes 2-butene, and the dimerization unit effluent is passed to the second fractionation train to produce a 2-butene stream. In embodiments where the dimerization unit effluent includes 2-butene and by-products and where the metathesis reactor effluent includes propylene, unconverted ethylene, and unconverted 2-butene, the process for passing the metathesis reactor effluent to the third fractionation train to recover the propylene may also include recovering the unconverted ethylene and unconverted 2-butene along with the propylene. In addition, the process for converting alkanes includes providing a propylene plant having a metathesis reactor and a third fractionation train. In selected embodiments, the polypropylene plant also includes hydrocarbon-fueled heaters and/or boilers, wherein the oxygen enhanced combustion is employed to limit nitrogen-based gas volumes. At the propylene plant, the 2-butene stream and a portion of the second ethylene stream is converted in the metathesis reactor to produce a metathesis reactor effluent which includes propylene, and the metathesis reactor effluent is passed to the third fractionation train to recover the propylene. The disclosed process also includes polymerizing the propylene (and optionally, the ethylene) in a polypropylene plant. By polymerizing the propylene (and the ethylene) in the polypropylene plant while applying a propylene polymerization technology, using renewable electric power, and scrubbing carbon dioxide from any fired heater or boiler stack gasses, the processing steps result in substantially zero carbon dioxide atmospheric emissions. In selected embodiments where the natural gas includes methane and the oxidation reactor effluent includes unconverted methane, the disclosed process may include recycling a stream of the unconverted methane from the first fractionation train to the oxidation reactor. In selected embodiments where the dimerization unit effluent includes unconverted ethylene, the disclosed process may include recycling a stream of unconverted ethylene from the second fractionation train to the dimerization unit. In selected embodiments where the metathesis reactor effluent includes unconverted ethylene and unconverted 2-butene, the disclosed process may include recycling a stream of unconverted ethylene and unconverted 2-butene from the third fractionation train to the metathesis reactor.

While these embodiments have been described with emphasis on the embodiments, it should be understood that within the scope of the appended claims, the embodiments might be practiced other than as specifically described herein.

What is claimed is:

1. A substantially zero carbon dioxide emissions process for making propylene polymers and copolymers comprising:
   a. converting alkanes to ethylene, propylene, and butene using renewable electric power in an oxidative-coupling of methane (OCM) plant comprising an ethylene plant, a 2-butene plant, and a propylene plant, comprising:
      i. providing an ethylene plant comprising an oxidation reactor and a first fractionation train and converting natural gas and oxygen in the oxidation reactor to produce an oxidation reactor effluent comprising ethylene and passing the oxidation reactor effluent to the first fractionation train to recover a first ethylene stream, a second ethylene stream, and a third ethylene stream;
      ii. providing a 2-butene plant comprising a dimerization unit and a second fractionation train and converting a portion of the first ethylene stream in the dimerization unit to produce a dimerization unit effluent comprising 2-butene and passing the dimerization unit effluent to the second fractionation train to produce a 2-butene stream;
      iii. providing a propylene plant comprising a metathesis reactor and a third fractionation train and converting the 2-butene stream and a portion of the second ethylene stream in the metathesis reactor to produce a metathesis reactor effluent comprising propylene and passing the metathesis reactor effluent to the third fractionation train to recover the propylene; and b. polymerizing the propylene and, optionally, the third ethylene stream in a polypropylene plant while applying a propylene polymerization technology, using renewable electric power, and scrubbing carbon dioxide from any fired heater or boiler stack gasses, thereby emitting substantially zero carbon dioxide atmospheric emissions.

2. The process of claim 1, wherein the natural gas comprises methane and the oxidation reactor effluent comprises unconverted methane, and further comprising recycling a stream of the unconverted methane from the first fractionation train to the oxidation reactor.

3. The process of claim 2, wherein the dimerization unit effluent comprises unconverted ethylene, and further comprising recycling a stream of unconverted ethylene from the second fractionation train to the dimerization unit.

4. The process of claim 3, wherein the metathesis reactor effluent comprises unconverted ethylene and unconverted 2-butene, and further comprising recycling a stream of unconverted ethylene and unconverted 2-butene from the third fractionation train to the metathesis reactor.

5. The process of claim 1, wherein converting the natural gas and oxygen in the oxidation reactor to produce the oxidation reactor effluent comprising ethylene comprises contacting a catalyst in the oxidation reactor with oxygen and the natural gas at a pressure from 6 bar to 16 bar and a temperature of 600 to 800 degree C. to produce the oxidation reactor effluent, wherein: (i) the catalyst is selected from the group consisting of a lanthanide series metal supported catalyst and an actinide series metal supported catalyst; (ii) the natural gas comprises a mixture of alkanes; and (iii) the oxidation reactor effluent comprises ethylene and carbon dioxide.

6. The process of claim 5, wherein the dimerization unit effluent comprises 2-butene and by-products.

7. The process of claim 6, wherein the metathesis reactor effluent comprises propylene, unconverted ethylene, and unconverted 2-butene and wherein passing the metathesis reactor effluent to the third fractionation train to recover the propylene further comprises recovering the unconverted ethylene and unconverted 2-butene along with the propylene.

8. The process of claim 1, wherein the polypropylene plant further comprises hydrocarbon-fueled heaters and/or boilers, wherein the oxygen enhanced combustion is employed to limit nitrogen-based gas volumes.

* * * * *